United States Patent
Sanders et al.

(10) Patent No.: US 9,498,637 B2
(45) Date of Patent: Nov. 22, 2016

(54) WEARABLE COLD PLASMA SYSTEM

(71) Applicant: Plasmology4, Inc., Scottsdale, AZ (US)

(72) Inventors: Roy W. Sanders, Tampa, FL (US);
David J. Jacofsky, Peoria, AZ (US);
Steven A. Myers, Scottsdale, AZ (US);
Jeffrey I. Meyers, Phoenix, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 202 days.

(21) Appl. No.: 14/292,158

(22) Filed: May 30, 2014

(65) Prior Publication Data

US 2015/0343231 A1    Dec. 3, 2015

(51) Int. Cl.
| | | |
|---|---|---|
| *A61N 1/44* | (2006.01) | |
| *A61B 18/04* | (2006.01) | |
| *H05H 1/24* | (2006.01) | |
| *A61M 35/00* | (2006.01) | |
| *A61L 2/14* | (2006.01) | |
| *A61B 18/00* | (2006.01) | |

(52) U.S. Cl.
CPC ............... *A61N 1/44* (2013.01); *A61B 18/042* (2013.01); *H05H 1/2406* (2013.01); *A61B 2018/00452* (2013.01); *A61L 2/14* (2013.01); *A61M 35/00* (2013.01); *H05H 2001/2418* (2013.01); *H05H 2001/2425* (2013.01); *H05H 2245/122* (2013.01); *H05H 2245/125* (2013.01); *H05H 2277/10* (2013.01)

(58) Field of Classification Search
None
See application file for complete search history.

(56) References Cited

U.S. PATENT DOCUMENTS

| | | | | |
|---|---|---|---|---|
| 5,961,772 A * | 10/1999 | Selwyn | ............. | H01J 37/32192 118/723 ER |
| 6,262,523 B1 * | 7/2001 | Selwyn | ............. | H01J 37/32009 313/231.31 |
| 6,441,554 B1 * | 8/2002 | Nam | ........................ | A61L 9/22 118/723 R |
| 6,831,421 B1 * | 12/2004 | Bletzinger | ............. | B01D 53/32 315/207 |
| 7,491,429 B2 * | 2/2009 | De Vries | ............... | C23C 16/503 118/715 |
| 7,633,231 B2 * | 12/2009 | Watson | .................... | H05H 1/46 219/121.36 |
| 7,791,281 B2 * | 9/2010 | Aldea | ............... | H01J 37/32174 118/723 E |
| 7,812,307 B2 * | 10/2010 | Dutton | ............. | H01J 37/32366 250/288 |
| 7,969,095 B2 * | 6/2011 | De Vries | ........... | H01J 37/32174 118/723 E |
| 8,124,013 B1 * | 2/2012 | Gregoire | .................. | H05H 1/46 204/157.15 |
| 8,136,481 B2 * | 3/2012 | Viol | ..................... | H05H 1/2406 118/723 E |

(Continued)

FOREIGN PATENT DOCUMENTS

WO    2012106735 A2    8/2012

OTHER PUBLICATIONS

PCT Invitation to Pay Additional Fees; Application No. PCT/US2015/033390; Dated Sep. 23, 2015; 6 pages.

(Continued)

*Primary Examiner* — Alexander H Taningco
*Assistant Examiner* — Srinivas Sathiraju
(74) *Attorney, Agent, or Firm* — Fletcher Yoder, P.C.

(57) ABSTRACT

A system including a wearable cold plasma system, including a wearable cold plasma applicator configured to couple to and deliver a cold plasma to a surface of a user wearing the wearable cold plasma device.

30 Claims, 10 Drawing Sheets

(56) References Cited

U.S. PATENT DOCUMENTS

| | | | | |
|---|---|---|---|---|
| 8,277,616 B2* | 10/2012 | Liu | ............................ | A61C 5/00 204/164 |
| 8,857,371 B2* | 10/2014 | Tabata | .................... | C23C 16/505 118/723 E |
| 8,896,211 B2* | 11/2014 | Ish-Yamini Tomer | ... | H05H 1/24 315/111.21 |
| 9,006,976 B2* | 4/2015 | Watson | .................. | A61M 16/12 315/111.21 |
| 9,064,674 B2* | 6/2015 | Ouyang | .................. | H01J 49/105 |
| 2009/0009090 A1* | 1/2009 | Viol | ....................... | H05H 1/2406 315/111.21 |
| 2010/0087812 A1* | 4/2010 | Davison | .............. | A61B 18/1402 606/41 |
| 2011/0018444 A1* | 1/2011 | Pouvesle | .............. | H05H 1/2406 315/111.21 |
| 2011/0180149 A1* | 7/2011 | Fine | ........................ | B01J 21/063 137/1 |
| 2011/0180732 A1* | 7/2011 | Hirasawa | .................. | A61N 1/44 250/492.3 |
| 2012/0046597 A1 | 2/2012 | Morfill et al. | | |
| 2012/0046602 A1* | 2/2012 | Morfill | .................. | A61L 2/0011 604/23 |
| 2012/0259270 A1* | 10/2012 | Wandke | ................ | A61N 1/0408 604/23 |
| 2012/0271225 A1* | 10/2012 | Stieber | .................. | A61B 18/042 604/26 |
| 2012/0296265 A1* | 11/2012 | Dobrynin | ............. | A61N 1/0468 604/23 |
| 2013/0022514 A1 | 1/2013 | Morfill et al. | | |
| 2013/0072858 A1* | 3/2013 | Watson | .................. | A61M 16/12 604/23 |
| 2013/0072859 A1* | 3/2013 | Watson | .................. | A61M 16/12 604/23 |
| 2013/0072861 A1 | 3/2013 | Watson et al. | | |
| 2013/0204244 A1* | 8/2013 | Sakakita | ............... | A61B 18/042 606/40 |
| 2013/0345620 A1* | 12/2013 | Zemel | .................. | A61B 18/042 604/24 |
| 2014/0197732 A1* | 7/2014 | Schultz | ................ | H05H 1/2406 315/111.21 |

OTHER PUBLICATIONS

PCT International Search Report; Application No. PCT/US2015/033390; Dated Dec. 3, 2015; 6 pages.

* cited by examiner

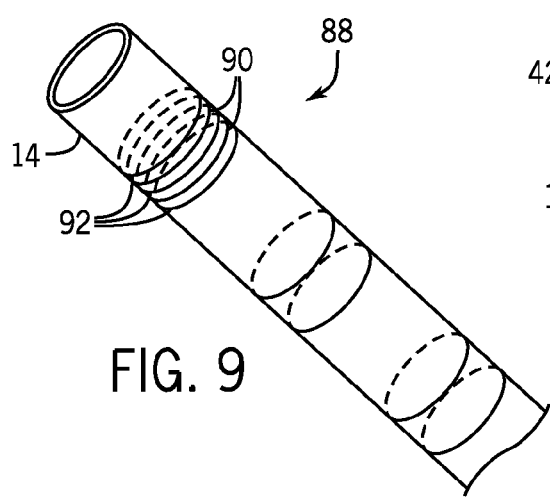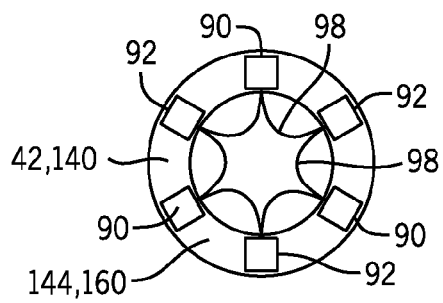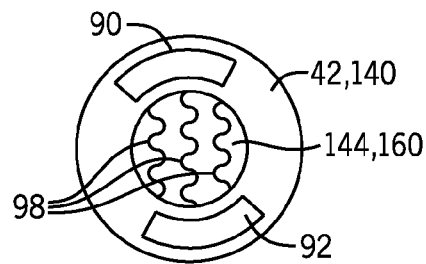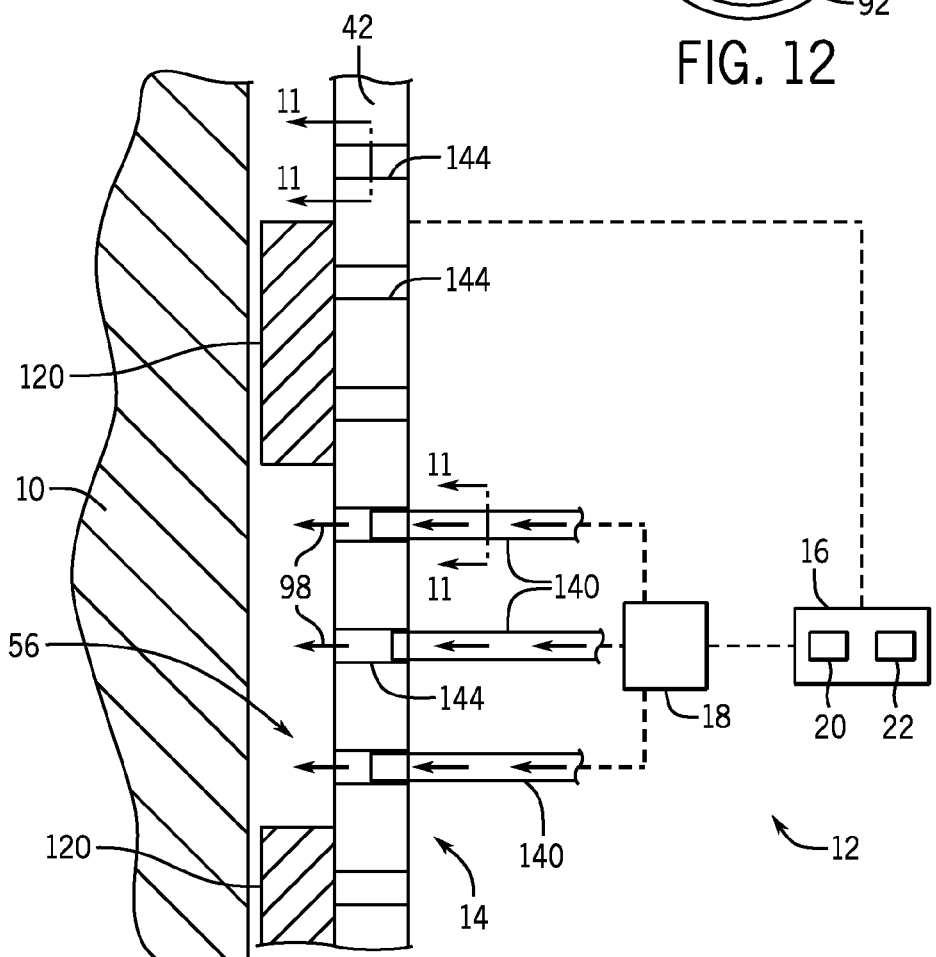

WEARABLE COLD PLASMA SYSTEM

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Modern medicine enables physicians to treat a wide variety of wounds and infections on a patient. For example, physicians may treat these wounds and infections using topical medication (e.g., creams, foams, gels, ointments, bandages, etc.) and/or internal medication (e.g., medicine administered orally, intravenously). Unfortunately, existing treatments may be costly, ineffective, and/or slow to treat certain wounds and infections.

BRIEF SUMMARY

A wearable cold plasma system may include a wearable cold plasma applicator configured to provide a cold plasma to a surface of a user. The wearable cold plasma applicator may be configured to conform to the surface. For example, the wearable cold plasma applicator may include one or more flexible layers, such as a fluid filled layer. The fluid filled layer may include, for example, a liquid filled layer or a layer with conductive particles in a fluid. The wearable cold plasma system may include a plurality of modular interchangeable plasma application sections configured to selectively couple together to change a configuration of the wearable cold plasma applicator. The wearable cold plasma applicator may include one or more apertures each associated with one or more electrodes, and the one or more electrodes may be configured to generate the cold plasma with a fluid flow through each respective aperture of the one or more apertures.

BRIEF DESCRIPTION OF THE DRAWINGS

Various features, aspects, and advantages of the present invention will become better understood when the following detailed description is read with reference to the accompanying figures in which like characters represent like parts throughout the figures, wherein:

FIG. 9 is a perspective view of an embodiment of a wearable cold plasma applicator using a cascade DBD;

FIG. 10 is a cross-sectional side view of an embodiment of a wearable cold plasma applicator coupled to a gas source;

FIG. 11 is a cross-sectional view of an embodiment of electrodes in a conduit or a wearable cold plasma applicator taken along line 11-11 of FIG. 10;

FIG. 12 is a cross-sectional view of an embodiment of electrodes in a conduit or a wearable cold plasma applicator taken along line 11-11 of FIG. 10;

DETAILED DESCRIPTION OF SPECIFIC EMBODIMENTS

One or more specific embodiments of the present invention will be described below. These described embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The disclosed embodiments include a wearable cold plasma system capable of forming a non-thermal plasma for treating exterior wounds, infections, cancers, and other conditions (e.g., systemic lupus, erythematosus, cutaneous lupus erythematosus, scleroderma, psoriasis, dermatomyositis, dermatitis, musculoskeletal diseases or disorders associated with an acute injury, chronic injury, chronic joint pain or an autoimmune or inflammatory disease or disorder). To facilitate treatment, the wearable cold plasma system may be formed into a wearable applicator that aids in placement and focuses the treatment on areas of interest (e.g., a treatment site). In some embodiments, the wearable cold plasma system may conform to the shape of the wound/infection site (e.g., arm, leg, chest, hand, neck, etc.) enabling more effective treatments. For example, the wearable cold plasma system may be formed into a glove, sleeve, patch, bandage, boot, sock, pants, shirt, headband, hood, etc. Accordingly, the wearable cold plasma system may enable targeted and uniform treatment of an entire wound or infection site.

Figure 1:
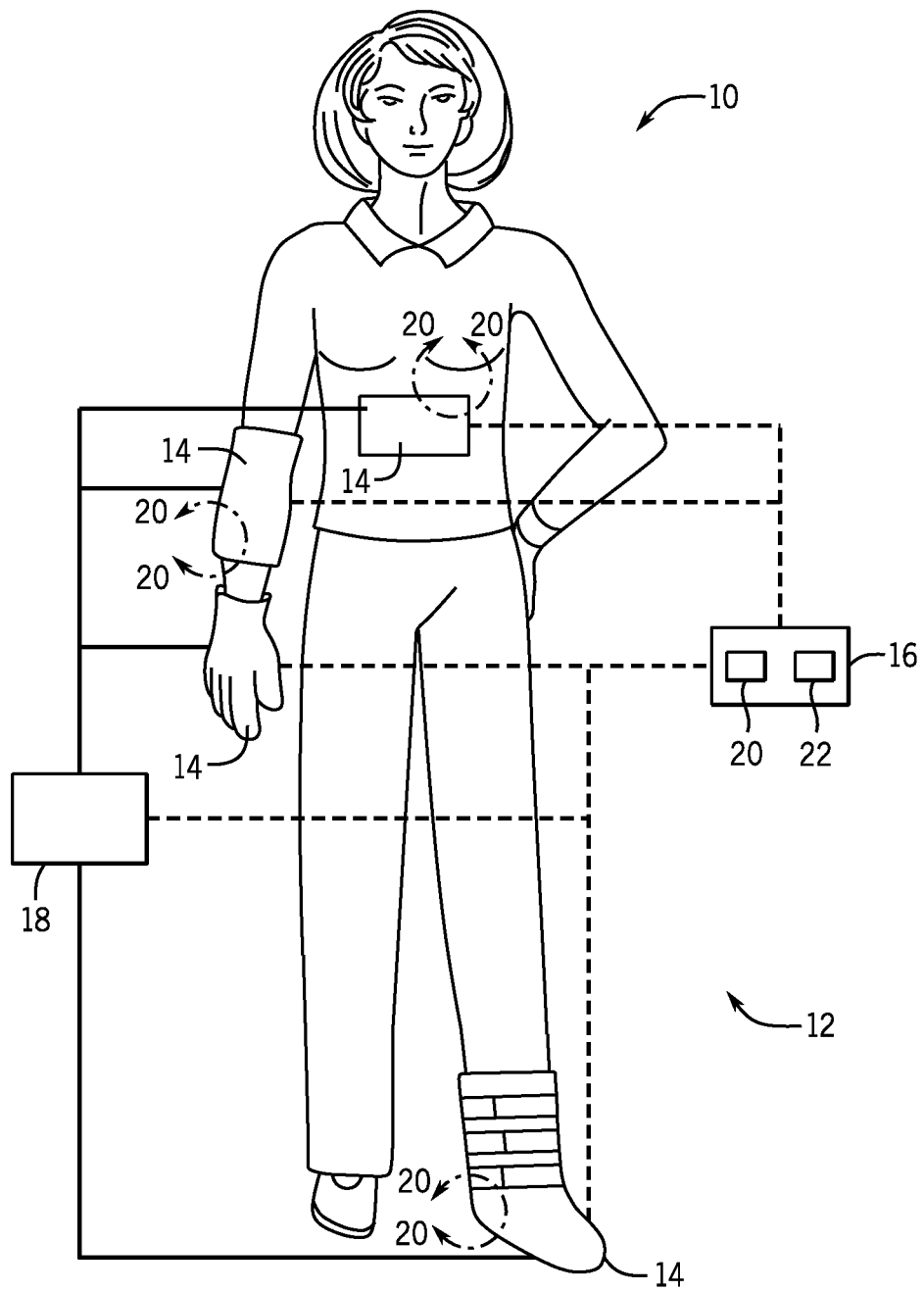
FIG. 1 is a front view of an embodiment of a wearable cold plasma system coupled to a patient.

FIG. 1 is a front view of an embodiment of a patient 10 with a wearable cold plasma system 12. The wearable cold plasma system 12 may include a wearable cold plasma applicator 14, a controller 16, and a gas source 18. As illustrated, the wearable cold plasma applicator 14 may be formed into a wearable module (e.g., article of clothing) such as a sleeve, a patch (e.g., a medical patch, bandage, sheet, etc.), a boot, a glove, etc. that enables easy attachment to a patient 10 for treatment. In operation, the wearable cold plasma applicator 14 may receive cold plasma from the gas source 18 or enable the wearable cold plasma system 12 to form cold plasma with atmospheric air next to the skin of the patient 10. For example, in embodiments using a gas from the gas source 18, the controller 16 sends an electrical signal that enables the gas source 18 to produce cold plasma used by the wearable cold plasma applicator 14. In another embodiment, the wearable cold plasma applicator 14 may receive an electrical signal that enables the wearable cold plasma applicator 14 to produce cold plasma from atmospheric gases next to the patient's skin, or with gas from the gas source 18.

The controller 16 uses a processor 20 to execute instructions stored in a memory 22 to start the flow of gas from the gas source 18 as well as produce and control a cold plasma generating electrical signal (e.g., change power, amplitude, frequency/frequencies, pulse timing, etc.). In some embodiments, the electrical signal may be a multi-frequency harmonic-rich signal (e.g., a timed pulse electrical signal that is pulsed between 100-700 Hz with an output voltage between 1-30 kV having multiple A/C waves at multiple frequencies that overlap to produce 100,000-2,000,000 or more harmonic components between DC and 400 MHz). As the multi-frequency, harmonic-rich electrical signal passes through the gas (e.g., gas in the gas source 18 or atmospheric gases); the gas molecules/atoms lose and gain electrons to produce cold plasma with positive ions, negative ions, and electrons. It is believed that the multi-frequency, harmonic-rich electrical signal facilitates removal of electrons from molecules/atoms with less energy than typical plasma formation. Accordingly, the plasma is a low temperature plasma or cold plasma (e.g., a cold plasma with a temperature between approximately 60-120, 60-80, 70-90, 80-100, 90-110, 100-120 degrees Fahrenheit), enabling exposure to a temperature sensitive target substrate 12 (e.g., biological tissue).

Figure 2:
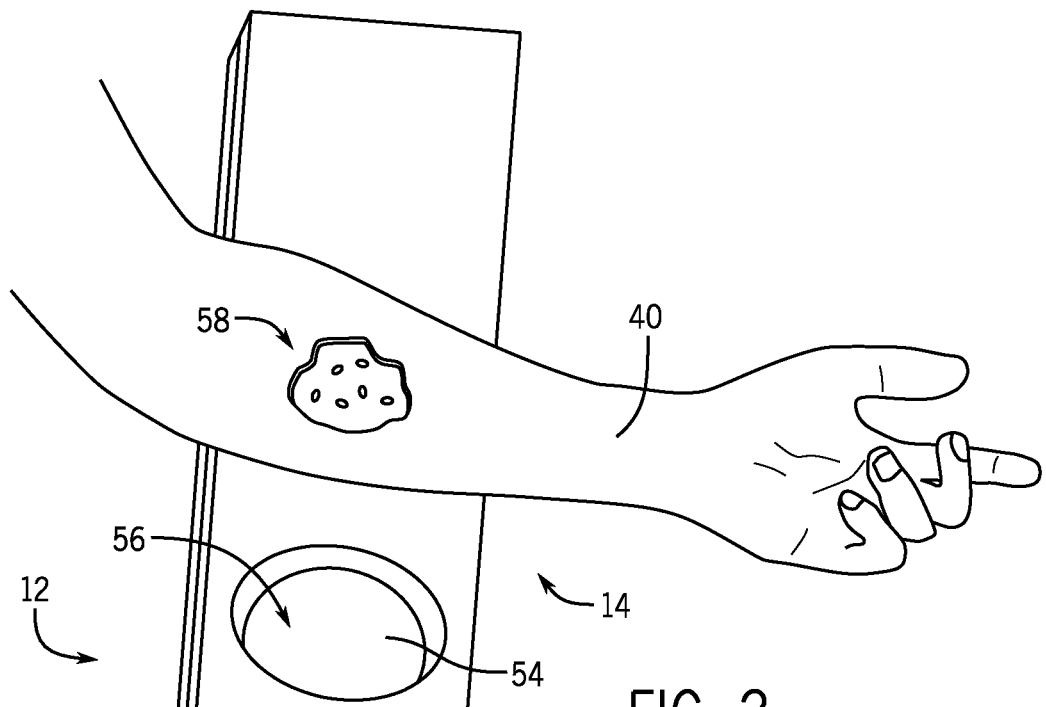
FIG. 2 is a perspective view of an embodiment of an arm and a wearable cold plasma applicator.

FIG. 2 is a perspective view of an embodiment of an arm 40 and a wearable cold plasma system 12. As explained above, the wearable cold plasma system 12 includes the controller 16 and the wearable cold plasma applicator 14. As illustrated, the wearable cold plasma applicator 14 includes a flexible dielectric barrier layer 42 (e.g., Silicone, Latex, open cell foam, gauze, hydrogels, PolyOxyMethylene, Polyamide, Polytetrafluoroethylene (PTFE), Acetal Homopolymer, Polyethylene (PE), Polypropylene (PP), Poly Vinyl Chloride (PVC), Ethylene Vinyl Acetate (EVA), Propylene, Copolyster Ether, and Polyolefin film) coupled to a flexible fluid filled layer 44. In some embodiments, the fluid filled layer 44 may be a multi-phase fluid (e.g., solid/gas, solid/liquid, gas/liquid, solid/gas/liquid) that includes conductive material 46 (e.g., conductive particles) in a fluid 48 (e.g., gas and/or liquid). The conductive material 46 may be a conductive non-ferromagnetic material (e.g., brass, copper, silver, aluminum, magnesium, platinum, carbon shavings, or dissolved salts) or a combination of non-ferromagnetic materials. In some embodiments, the conductive material 46 may be randomly or uniformly shaped, and have shapes that are helical, spherical, rectangular, elongated, curved, wavy, etc. The fluid 48 may be a working gas mixture that includes noble gases (e.g., helium, neon, argon, krypton, xenon, radon) or a combination of a noble gas(s) with atmospheric gases (e.g., oxygen, nitrogen). In some embodiments, the fluid 48 may be a liquid (e.g., a saline solution). The flexibility of the dielectric barrier layer 42 and the fluid filled layer 44 enables the wearable cold plasma applicator 14 to conform to the shape of a patient's body as well as the treatment/wound site for more effective treatment on a variety of patients and anatomical sites. For example, wounds/infections may not be flat (e.g., deep wounds) or located on a flat portion of a patient's body. Accordingly, a wearable cold plasma applicator 14 that conforms to a patient's body as well as the treatment/wound site may be more effective in treating the treatment/wound site with cold plasma (e.g., focused uniform treatment across site). In some embodiments, the wearable cold plasma applicator 14 may be attached to a patient (e.g., wrapped, attached with a hook and loop, attached with an adhesive, etc.) before filling the fluid filled layer 44. By filling the fluid filled layer 44 after attachment, the wearable cold plasma applicator 14 may improve contact between dielectric barrier layer 42 and the patient's body and/or the treatment/wound site.

In operation, the electrical signal from the controller 16 passes through a cable 50 (e.g., HV/RF feed cables) to a conductive non-ferromagnetic wire electrode 52 (e.g., tungsten) in the flexible fluid filled layer 44. In some embodiments, there may be more than one conductive non-ferromagnetic wire electrode 52 (e.g., 1, 2, 3, 4, 5, 6, 7, 8, 9, 10, or more). Embodiments with more than one conductive non-ferromagnetic wire electrode 52, may enable each electrode 52 to carry a different electrical signal (e.g., signals may differ in number of waves, frequency, amplitude) or the same electrical signal. As the electrical signal enters the flexible fluid filled layer 44, the fluid 48 conducts the electrical signal through the flexible fluid filled layer 44 to one or more plasma generation regions 54 (e.g., locations where the dielectric barrier layer 42 is thinner, enabling the charge to pass through the dielectric barrier layer 42). It is in these plasma generation regions 54 that charge builds before crossing an air gap 56 between the dielectric barrier layer 42 and the patient's skin. Once a sufficient amount of charge builds in the plasma generation region 54, the multi-frequency harmonic-rich electrical signal crosses the air gap 56 to the patients skin (e.g., ground), forming cold plasma. As illustrated, the plasma generation region 54 is sized to completely surround the wound site 58. Accordingly, during use, the wearable cold plasma system 12 may be capable of treating the entire wound site 58 (e.g., killing pathogens, improving blood coagulation).

Figure 3:
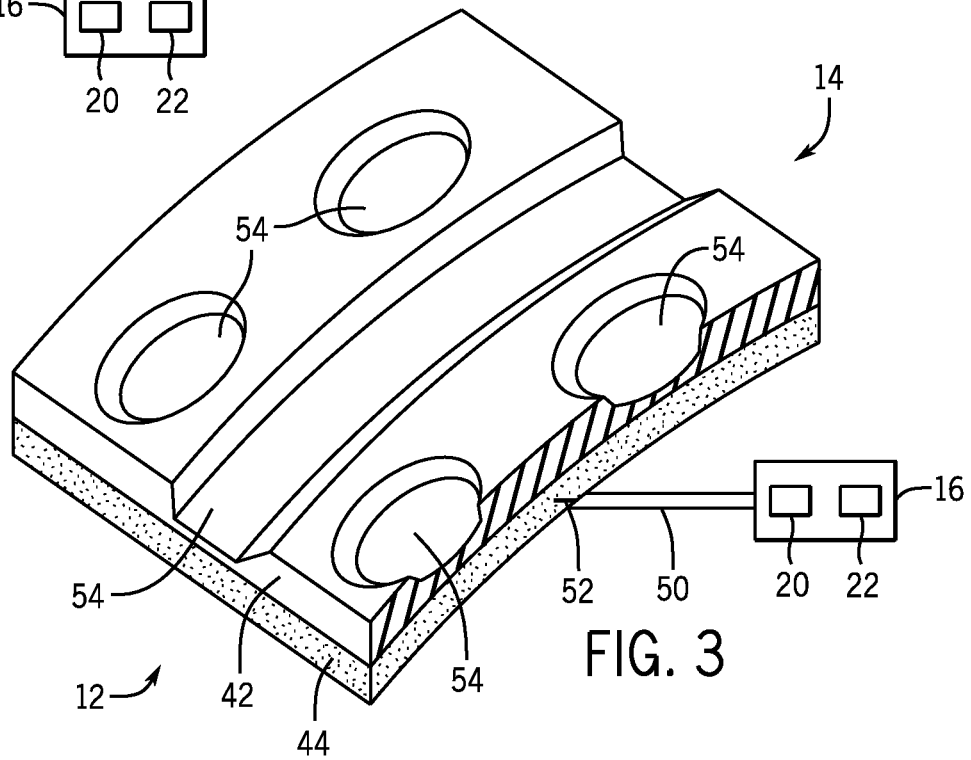
FIG. 3 is a perspective view of an embodiment of a wearable cold plasma applicator.

FIG. 3 is a perspective view of an embodiment of a wearable cold plasma system 14. As illustrated, the wearable cold plasma applicator 14 may have different plasma generation regions 54. As seen above in FIG. 2, the plasma generation region 54 may be sized to completely surround a treatment site 58. In other embodiments, such as shown in FIG. 3, the wearable plasma treatment applicator 14 may have multiple plasma generation areas 54 that enable treatment of multiple treatment sites 58. In these embodiments, the wearable plasma generation applicator 14 may have many plasma generation regions 54 (e.g., 10, 50, 100, 1000, 10000 or more) that are in close proximity to each other enabling a plasma treatment over a large area. Furthermore, in some embodiments, the wearable cold plasma applicator 14 may have plasma treatment regions 54 that have a variety of different sizes and shapes for treating different regions of a patient's body (e.g., circular, oval, square, rectangular, irregular). For example, the wearable cold plasma applicator 14 may include a plasma generation region 54 that forms a large channel for treatment of a site that is proportionally narrow but long. Accordingly, the wearable cold plasma applicator 14 may include multiple plasma generation regions 54 that enable treatments of multiple sites and anatomical features (e.g., fingers, toes, joints, feet, legs, arms, chest, neck, etc.)

Figure 4:
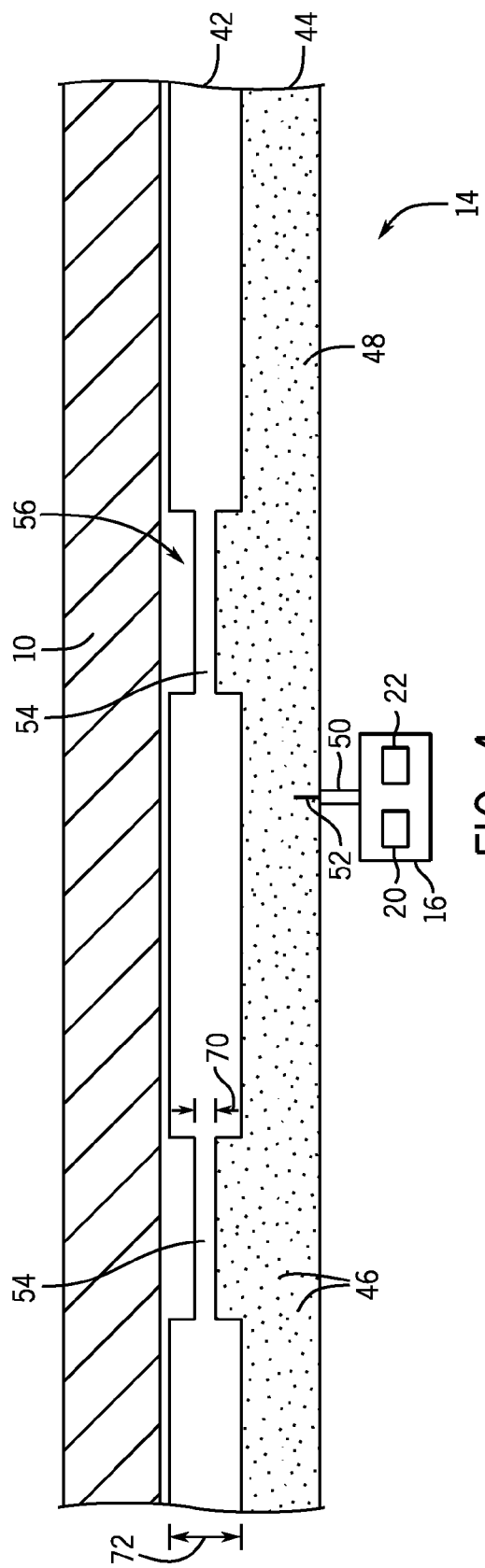
FIG. 4 is a cross-sectional side view of an embodiment of a wearable cold plasma applicator using a fluid-based dielectric barrier discharge (DBD)

FIG. 4 is a cross-sectional side view of an embodiment of the wearable cold plasma system in FIGS. 1-3. As explained above, the wearable cold plasma applicator 14 includes a flexible dielectric barrier layer 42 (e.g., Silicone, Latex, open cell foam, gauze, hydrogels, PolyOxyMethylene, Polyamide, Polytetrafluoroethylene (PTFE), Acetal Homopolymer, Polyethylene (PE), Polypropylene (PP), Poly Vinyl Chloride (PVC), Ethylene Vinyl Acetate (EVA), Propylene, Copolyster Ether, and Polyolefin film) coupled to flexible fluid filled layer 44. In some embodiments, the fluid filled layer 44 may be a multi-phase fluid that includes conductive material 46 in a fluid 48 (e.g., gas and/or liquid). The flexibility of the dielectric barrier layer 42 and the fluid filled layer 44 enables the wearable cold plasma applicator 14 to conform to the shape of a patient's body for more effective treatment on a variety of patients and anatomical sites.

In operation, the electrical signal from the controller 16 passes through the cable 50 (e.g., HV/RF feed cables) to the conductive non-ferromagnetic wire electrode 52 (e.g., tungsten) in the flexible fluid filled layer 44. As the electrical signal enters the flexible fluid filled layer 44, the fluid 48 conducts the electrical signal through the flexible fluid filled layer 44 to the plasma generation region(s) 54. As illustrated, the plasma generation regions 54 have a thickness 70, while the rest of the dielectric barrier layer 42 has a thickness 72 greater than the thickness 70. It is in these plasma generation regions 54, where the dielectric barrier layer 42 has the thickness 70, that charge is able to build before crossing the air gap 56. In other words, the dielectric barrier layer 42 has a thickness of 72 to block charge movement except through the plasma generation regions 54. Once a sufficient amount of charge builds in the plasma generation region 54, the multi-frequency harmonic-rich electrical signal crosses the air gap 56 to the patients skin (e.g., ground), forming cold plasma.

Figure 5:
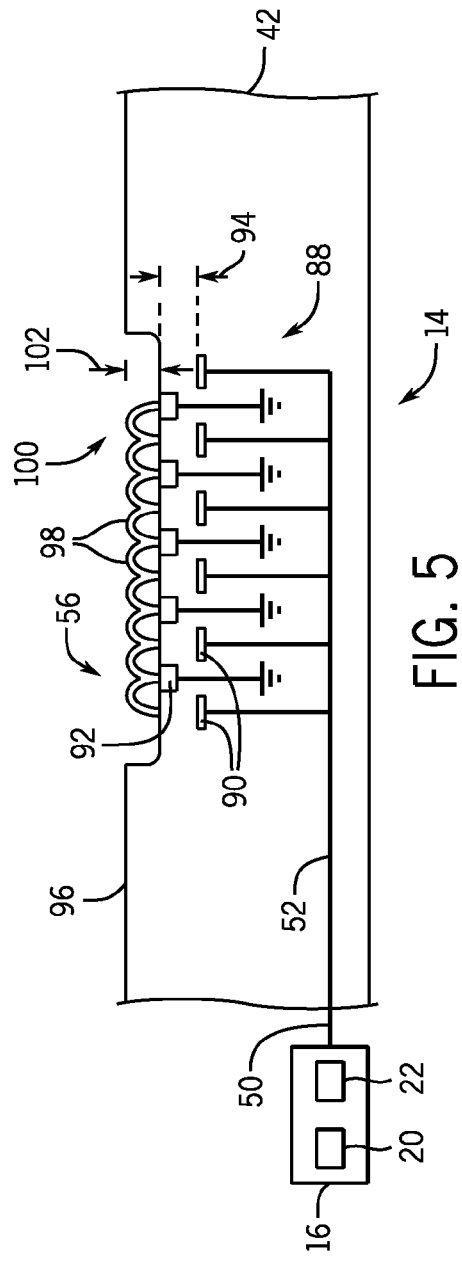
FIG. 5 is a cross-sectional side view of an embodiment of a wearable cold plasma applicator using a cascade DBD.

FIG. 5 is a cross-sectional side view of an embodiment of the wearable cold plasma system 12 in FIGS. 1-3. As explained above, the wearable cold plasma applicator 14 includes a flexible dielectric barrier layer 42 (e.g., Silicone, Latex, open cell foam, gauze, hydrogels, PolyOxyMethylene, Polyamide, Polytetrafluoroethylene (PTFE), Acetal Homopolymer, Polyethylene (PE), Polypropylene (PP), Poly Vinyl Chloride (PVC), Ethylene Vinyl Acetate (EVA), Propylene, Copolyster Ether, and Polyolefin film). The flexibility of the dielectric barrier layer 42 enables the wearable cold plasma applicator 14 to conform to a patient's body for more effective treatment on a variety of patients and anatomical sites. However, instead of a flexible fluid filled layer 44 that conducts the electrical signal, the wearable cold plasma applicator 14 of FIG. 5 includes a cascade dielectric barrier discharge (DBD) system 88 embedded in the dielectric barrier layer 42. The cascade DBD system 88 includes a non-ferromagnetic wire electrode 52 (e.g., tungsten), powered electrodes 90, and grounded electrodes 92 that enable the wearable cold plasma applicator 14 to form cold plasma in the air gap 56.

In operation, the controller 16 produces the cold plasma generating electrical signal that travels through the cable 50 (e.g., HV/RF feed cables) and the non-ferromagnetic wire electrode 52 (e.g., tungsten) to the powered electrodes 90. As illustrated, the powered electrodes 90 are a distance 94 away from the top surface 96 of the dielectric barrier layer 42, enabling charge to build on the electrode 90. Once a sufficient amount of charge builds on the electrode 90, the multi-frequency harmonic-rich electrical signal crosses the air gap 56 to the grounded electrodes 92, forming cold plasma 98. To ensure a sufficient air gap 56 between the patient 10 and the wearable cold plasma applicator 14, the dielectric barrier layer 42 may have a recess 100 in the top surface. The depth 102 of the recess 100 provides a sufficient amount of atmospheric air for cold plasma formation, while simultaneously enabling the cold plasma 98 to contact the patient for treatment. The recesses 100, like the plasma generating regions 54, may have a variety of different sizes and shapes for treating different regions of a patient's body (e.g., circular, oval, square, rectangular, irregular). For example, the wearable cold plasma applicator 14 may include a recess 100 that forms a large channel for treatment of a wound that is proportionally narrow but long. Accordingly, the wearable cold plasma applicator 14 may include multiple recesses 100 that enable treatments of multiple sites and anatomical features (e.g., fingers, toes, joints, feet, legs, arms, chest, neck, etc.)

Figure 6:
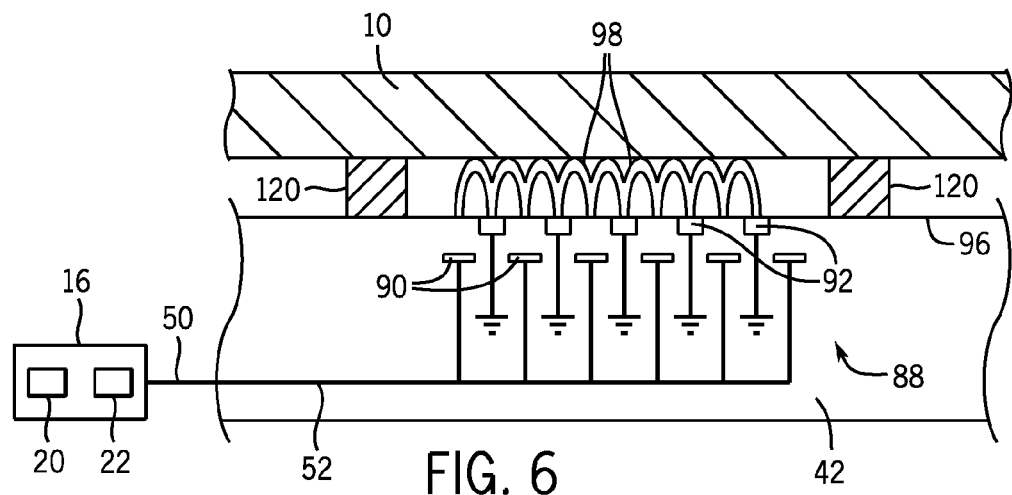
FIG. 6 is a cross-sectional side view of an embodiment of a wearable cold plasma applicator with spacers.

FIG. 6 is a cross-sectional side view of an embodiment of the wearable cold plasma system 12 in FIG. 1. As explained above, the wearable cold plasma applicator 14 includes a flexible dielectric barrier layer 42 (e.g., Silicone, Latex, open cell foam, gauze, hydrogels, PolyOxyMethylene, Polyamide, Polytetrafluoroethylene (PTFE), Acetal Homopolymer, Polyethylene (PE), Polypropylene (PP), Poly Vinyl Chloride (PVC), Ethylene Vinyl Acetate (EVA), Propylene, Copolyster Ether, and Polyolefin film). The flexibility of the dielectric barrier layer 42 enables the wearable cold plasma applicator 14 to conform to the shape of a patient's body for more effective treatment on a variety of patients and anatomical sites. The wearable cold plasma applicator 14, of FIG. 6, includes a cascade dielectric barrier discharge (DBD) system 88 embedded in the dielectric barrier layer 42. The cascade DBD system 88 includes the non-ferromagnetic wire electrode 52 (e.g., tungsten), powered electrodes 90, and grounded electrodes 92 that enable the wearable cold plasma applicator 14 to form cold plasma in the air gap 56. To ensure a sufficient air gap 56 between the patient 10 and the wearable cold plasma applicator 14, the wearable cold plasma applicator 14 may include spacers 120. The spacers 120 may be foam spacers, inflatable spacers, rigid spacers, or a combination thereof. The spacers 120 may also be fixed spacers and/or adjustable spacers. For example, the system 12 may include a plurality of differently sized spaces 120, which may be selectively attached to the applicator 14 to adjust the air gap 56. In operation, the spacers 120 help define the air gap 56 between the patient 10 and the dielectric barrier layer 42 that enables the cascade DBD system 88 to convert the atmospheric air into cold plasma 98.

Figure 7:
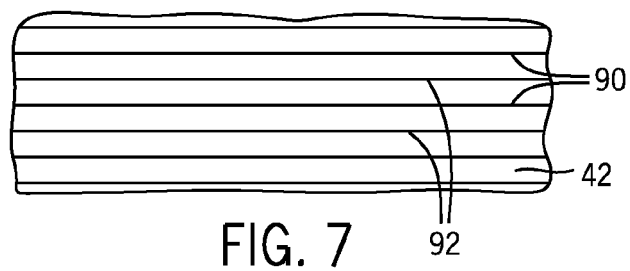
FIG. 7 is a top view of an embodiment of the cascade DBD illustrated in FIG. 6.
Figure 8:
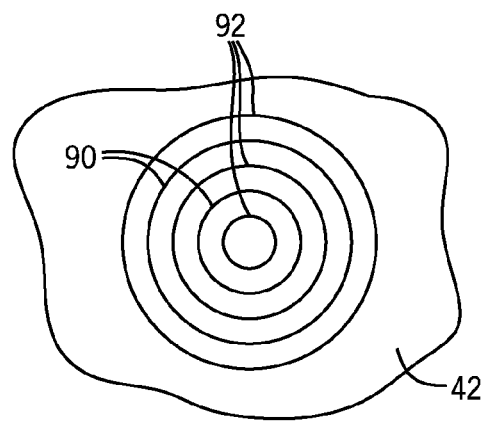
FIG. 8 is a top view of an embodiment of the cascade DBD illustrated in FIG. 6.

FIGS. 7 and 8 are top views of embodiments of the cascade DBD system 88 of FIG. 5 or 6. As illustrated, the cascade DBD system 88 may have a different layout for the electrodes 90 and 92. For example, in FIG. 7, the electrodes 90 and 92 are linear along a length of the dielectric barrier layer 42 (e.g., parallel electrodes). In FIG. 8, the electrodes 90 and 92 may be circular (e.g., concentric circular electrodes). However, in other embodiments, the electrodes may have different layouts (e.g., irregular). The layouts of the electrodes 90 and 92 in the cascade DBD system 88 may facilitate placement in different wearable cold plasma applicators 14 suited to different anatomical features.

FIG. 9 is a perspective view of an embodiment of a wearable cold plasma applicator 14 using a cascade DBD system 88. As illustrated, the wearable cold plasma applicator 14 may be in the form of a sleeve capable of surrounding a patient's appendage (e.g., a hand, finger, leg, arm, foot, toe, head, neck, chest, waist, etc.). Embedded in the wearable cold plasma applicator 14 is the cascade DBD system 88 that enables cold plasma generation about an entire circumference of a patient's body. Accordingly, instead of wrapping a portion of a patient 10, the wearable cold plasma applicator 14 may be pulled over the target area and then treated with cold plasma about an entire circumference. In some embodiments, the wearable cold plasma applicator 14 may be left on the patient 10 to shield the treatment site while enabling periodic cold plasma treatments (e.g., ten minutes every hour, twenty minutes every four hours).

FIG. 10 is a cross-sectional side view of an embodiment of a wearable cold plasma system 12 with an external gas source 18. In other words, the wearable cold plasma system 12 may not form cold plasma using atmospheric air near a patient's skin. Instead, the wearable cold plasma system 12 uses a working gas from the gas source 18. The gas may be a specific gas or mixture of gases (e.g., helium, neon, argon, krypton, xenon, radon, oxygen, nitrogen, or a combination thereof) that form different cold plasmas with properties ideally suited for specific treatments (e.g., a working gas that promotes faster wound healing, blood coagulation, infection treatment, etc.). As illustrated, the wearable cold plasma applicator 14 couples to the gas source 18 with conduits 140. The conduits 140 may be separately attachable to the wearable cold plasma applicator 14 or may be integrally formed as part of the wearable cold plasma applicator 14 (e.g., formed out of the same flexible material as the wearable cold plasma applicator 14). In an embodiment with separately attachable conduits 140, the wearable cold plasma applicator 14 may include multiple apertures 144 that couple to the conduits 140 (e.g., friction fit, snap fit, thread coupling, quick-release coupling, etc.).

As illustrated, the multiple apertures 144 may enable customized treatment of a target substrate. For example, if the treatment site is small, a user may couple only a smaller number of conduits 140 for cold plasma treatment. In contrast, if the treatment site is large, then a large number of conduits 140 may couple to the wearable cold plasma applicator 14 enabling more effective treatment of a larger area. In some embodiments, the wearable cold plasma applicator 14 may include spacers 120 (e.g., foam, inflatable, rigid spacers) that form the air gap 56. The spacers 120 may be anti-bacterial, non-stick, smooth, soft, sticky, or a combination thereof. In operation, the air gap 56, formed by the spacers 120, enables cold plasma propagation over the target substrate enabling treatment of a larger area with fewer conduits 140. The spacers 120 may also be positioned around a treatment site to help define the treatment site as well as ensure that the cold plasma is focused on the treatment site (e.g., block the spread of cold plasma to areas not requiring treatment).

In operation, the gas source 18 may form cold plasma using an electrical signal from the controller 16. As explained above, the electrical signal may be a multi-frequency harmonic-rich signal (e.g., a timed pulse electrical signal pulsed between 100-700 Hz with an output voltage between 1-30 kV having multiple A/C waves at multiple frequencies, that overlap to produce 100,000-2,000,000 or more harmonic components between DC and 400 MHz). As the multi-frequency harmonic-rich electrical signal passes through the gas, the gas molecules/atoms lose and gain electrons to produce a cold plasma with positive ions, negative ions, and electrons. The cold plasma may then be pumped through the conduits 140 and into the air gap 56 for patient treatment. In some embodiments, the gas source 18 may not form the cold plasma; instead, the cold plasma may be formed within the conduits 140. In other words, the cold plasma may be formed closer to the patient. For example, some or all of the conduits 140 may include electrodes. These electrodes may receive the electrical signal from the controller 16 enabling cold plasma formation within the conduits 140. In still other embodiments, the wearable cold plasma system 12 may form cold plasma at the gas source 18 and in the conduits 140 or increase ionization of gas in the conduits 140 after cold plasma formation by the gas source 18.

FIGS. 11 and 12 are cross-sectional views of an aperture 144 of a wearable cold plasma applicator 14 or an aperture 160 of the conduit 140. As illustrated, the electrodes 90 and 92 are embedded in layer 42 of the wearable cold plasma applicator 14 or in the material of the conduit 140 surrounding the apertures 144, 160. In operation, the powered electrodes 90 receive an electrical signal from the controller 16. Once a sufficient amount of charge builds on the electrode 90, the multi-frequency harmonic-rich electrical signal crosses through the gas in the aperture 144, 160 to the grounded electrode 92, forming the cold plasma 98. As illustrated in FIG. 11 the layer 42 or conduit 140 may include multiple electrodes 90, 92 (e.g., 2, 3, 4, 5, 6, 7, 8, 9, 10 or more) or only the two seen in FIG. 12. Moreover, in some embodiments with multiple electrodes 90, 92, the electrodes 90 and 92 may be placed axially (e.g., similar to FIG. 9) and/or circumferentially along the length of the aperture 144, 160. Furthermore, instead of including powered electrodes 90 and grounded electrodes 92, some embodiments may include only grounded electrodes 92. In operation, these grounded electrodes 92 may attract the cold plasma, reducing cold plasma dissipation as cold plasma travels through the conduit 140.

Figure 13:
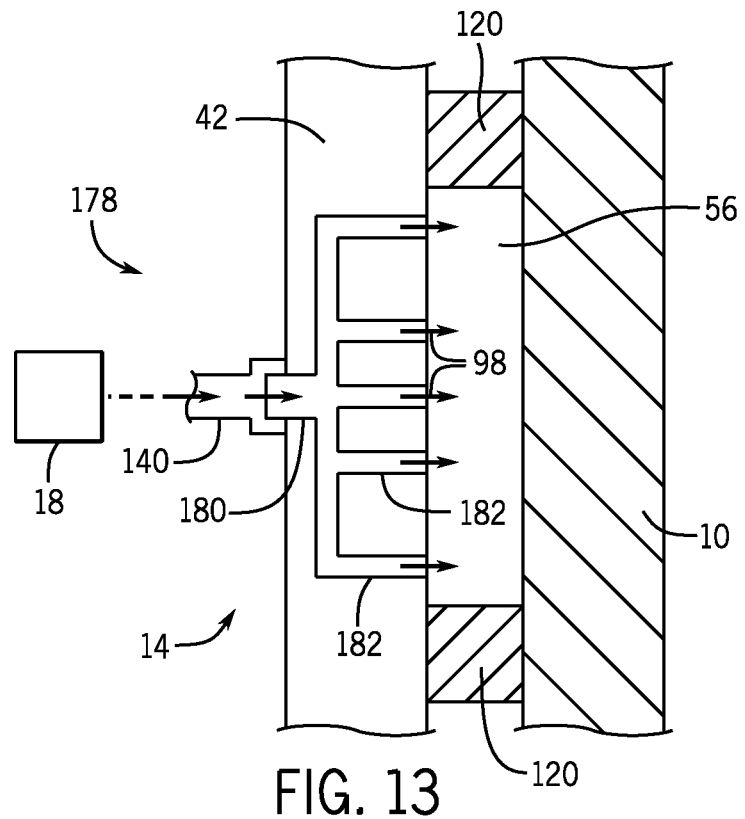
FIG. 13 is a cross-sectional side view of an embodiment of a wearable cold plasma applicator.

FIG. 13 is a cross-sectional side view of an embodiment of a wearable cold plasma applicator 14. In contrast to the wearable cold plasma applicator 14 illustrated in FIG. 10, the wearable cold plasma applicator 14 illustrated in FIG. 13 may reduce the number of external conduits 140 that provide gas/cold plasma to the wearable cold plasma applicator 14. As illustrated, the layer 42 of the wearable cold plasma applicator 14 may include a flow distribution manifold 178 having a main aperture 180 with multiple secondary apertures 182 coupled to the main aperture 180. In operation, the main aperture 180 receives gas/cold plasma from the gas source 18 traveling through the conduit 140. After passing through the main aperture 180, the gas/cold plasma enters the secondary apertures 182, which then guide and disperse the gas/cold plasma over a wider area. Accordingly, the wearable cold plasma system 12 may include fewer fluid conduits 140 between the gas source 18 and the wearable cold plasma applicator 14.

Figure 14:
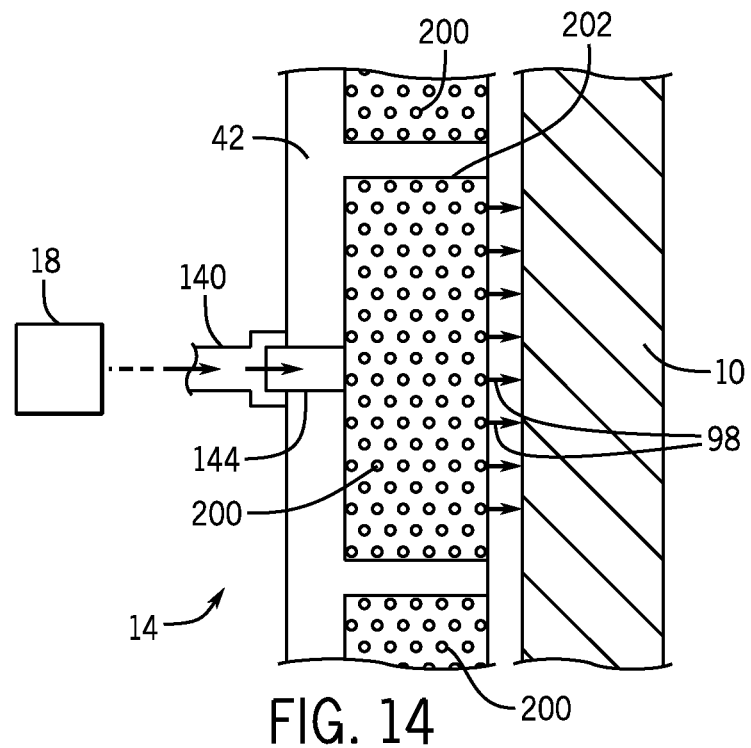
FIG. 14 is a cross-sectional side view of an embodiment of a wearable cold plasma applicator with porous material.

FIG. 14 is a cross-sectional side view of an embodiment of a wearable cold plasma applicator 14. In contrast to the wearable cold plasma applicator 14 illustrated in FIG. 10, the wearable cold plasma applicator 14 illustrated in FIG. 13 may reduce the number of external conduits 140 that provide gas/cold plasma to the wearable cold plasma applicator 14. As illustrated, the wearable cold plasma applicator 14 may include a flexible and/or porous material 200 (e.g., porous foam, porous fabric, porous plastic, porous gel) in a pocket 202 formed by the layer 42. In operation, the aperture 144 receives gas/cold plasma from the gas source 18 traveling through the conduit 140. After passing through the aperture 144, the gas/cold plasma enters the porous foam 200, which disperses the cold plasma 98 over a wider area during treatment. Accordingly, the wearable cold plasma system 12 may include fewer fluid conduits 140 between the gas source 18 and the wearable cold plasma applicator 14.

Figure 15:
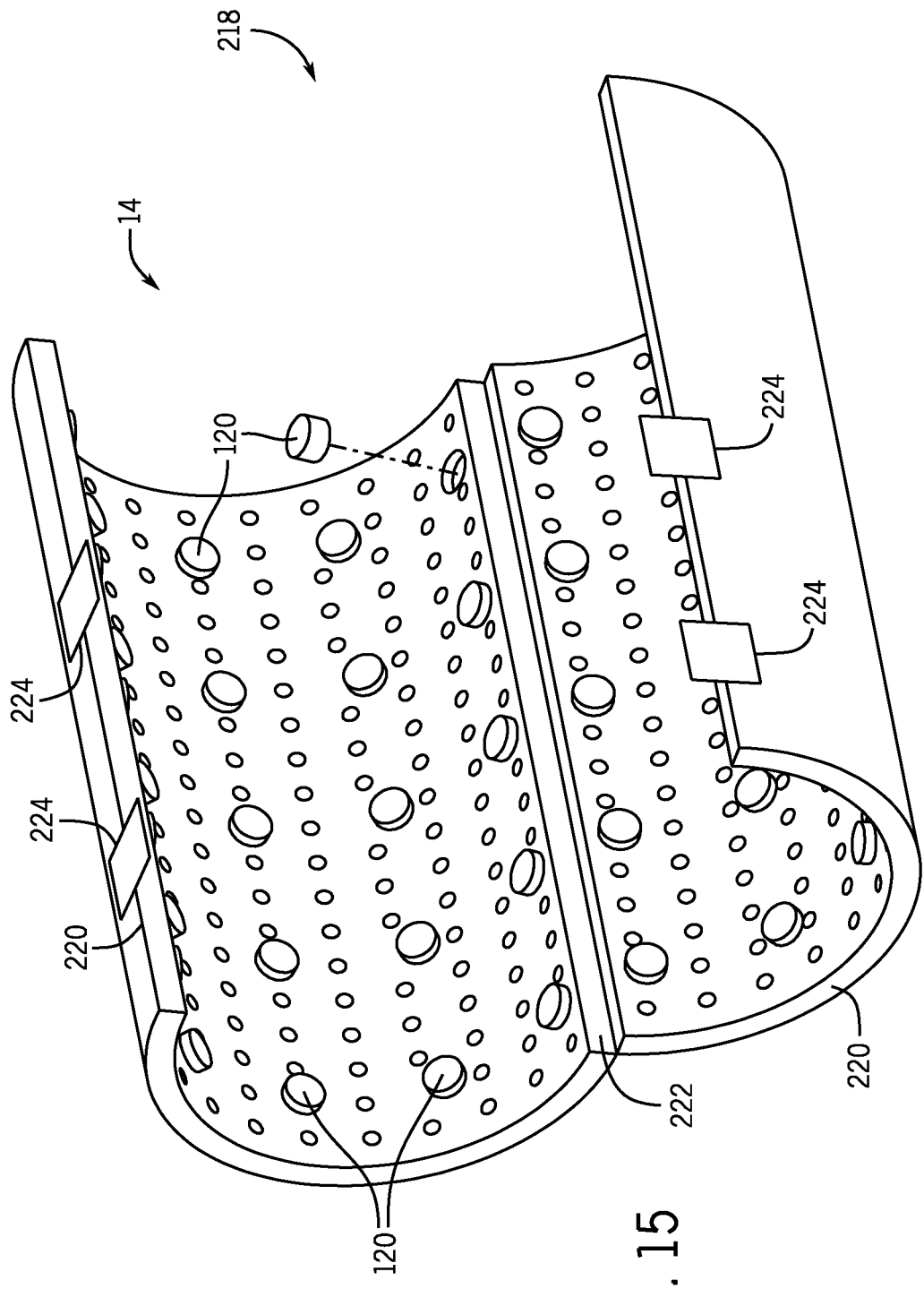
FIG. 15 is a perspective view of an embodiment of a wearable cold plasma applicator with spacers.

FIG. 15 is a perspective view of an embodiment of a wearable cold plasma applicator 14 with a segmented assembly 218. The segmented assembly 218 may include multiple sections 220 (e.g., 2, 3, 4, 5, 6, 7, 8, 9, 10, or more sections) that enable the wearable cold plasma applicator 14 to surround a target substrate (e.g., leg, neck, chest, foot, joint, finger, toe, etc.). The sections 220 may be formed from a flexible material (e.g., Silicone, Latex, open cell foam, gauze, hydrogels, PolyOxyMethylene, Polyamide, Polytetrafluoroethylene (PTFE), Acetal Homopolymer, Polyethylene (PE), Polypropylene (PP), Poly Vinyl Chloride (PVC), Ethylene Vinyl Acetate (EVA), Propylene, Copolyster Ether, and Polyolefin film) that molds to the target substrate, or a rigid/semi-rigid material. As illustrated, the wearable cold plasma applicator 14 may include two sections 220 that open and close with a hinge 222. In order to hold the wearable cold plasma applicator 14 in a closed position, the wearable cold plasma applicator 14 may include one or more fasteners 224 (e.g., hook-and-loop, hook-and-pile fasteners, snap fit, etc.). Once attached to a patient 10, the wearable cold plasma applicator 14 may generate cold plasma from atmospheric gases in air gaps between the spacers 120 like that discussed in FIGS. 2-8 or receive a specialized gas for conversion to cold plasma as discussed in FIGS. 10-14. As illustrated, the spacers 120 may be removable to facilitate changes in distance between the sections 220 and the target substrate. For example, in embodiments where the wearable cold plasma applicator 14 generates cold plasma with atmospheric gases between dielectric barrier discharge electrodes and the patient, the spacers 120 may be smaller to ensure that the electrodes and target substrate are close enough to generate cold plasma. In embodiments using a specialized gas, the spacers 120 may be larger to facilitate the spread of cold plasma over a surface of the target substrate. In either configuration, the wearable cold plasma applicator 14 enables treatment about an entire circumference of a target substrate.

Figure 16:
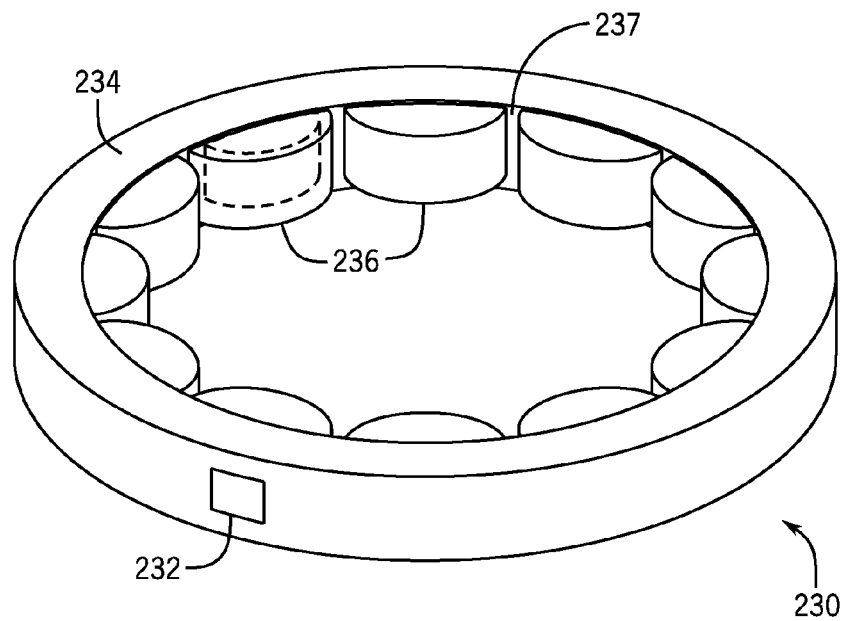
FIG. 16 is a perspective view of an embodiment of an inflatable cuff for use with the wearable plasma applicator of FIG. 15.

FIG. 16 is a perspective view of an embodiment of an inflatable cuff 230 (e.g., a spacer) for use with the wearable plasma applicator 14. As illustrated, the inflatable cuff 230 may include a fluid port 232 that receives a fluid (e.g., liquid or gas) that inflates a ring 234 and/or a plurality of protrusions 236. In operation, an external fluid source may pump a fluid into the inflatable cuff 230 filling the ring 234 and/or protrusions 236. As the protrusions 236 inflate, they force the ring 234 away from a target substrate. In this manner, the inflatable cuff 230 may form a secure connection between the wearable cold plasma applicator 14 and patient 10, as well as form the correct air gaps between the wearable cold plasma applicator 14 and the target substrate. In other words, the inflatable cuff 230 may replace or supplement the spacers 120 to provide the proper spacing while simultaneously securely positioning the wearable cold plasma applicator 14. In some embodiments, there may be gaps 237 between the protrusions that enable gas/plasma to escape during treatment, thus blocking over pressurization of the treatment site.

Figure 17:
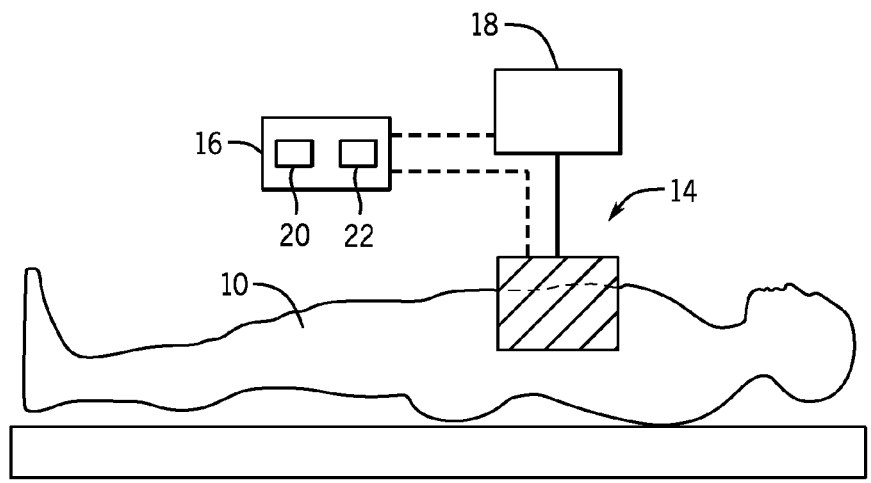
FIG. 17 is a side view of an embodiment of a wearable cold plasma applicator.
Figure 18:
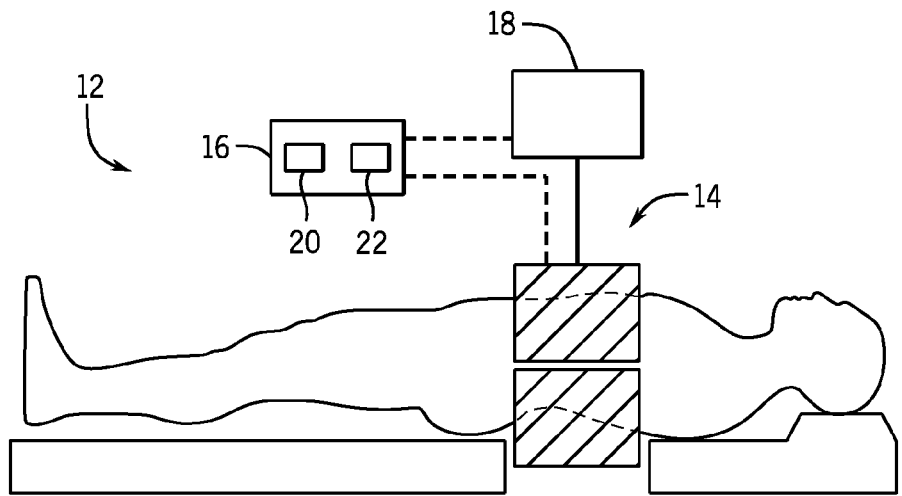
FIG. 18 is a side view of an embodiment of a wearable cold plasma applicator.

FIGS. 17 and 18 are side views of an embodiment of a wearable cold plasma system 12. As illustrated, in FIG. 17 the wearable cold plasma applicator 14 may be large enough to cover a patient's torso enabling a cold plasma treatment over a large area. For example, the wearable cold plasma applicator 14 may be a movable chamber or sheet that enables treatment of a significant portion of a patient. As explained above, the wearable cold plasma applicator 14 may form cold plasma using atmospheric air between the patient 10 or receive a specialized gas from the gas source 18 that is formed into cold plasma. In some embodiments, the cold plasma applicator 14 may be a segmented enclosure (e.g., clamshell) that surrounds the entire torso of the patient for a cold plasma treatment, as illustrated in FIG. 18.

Figure 19:
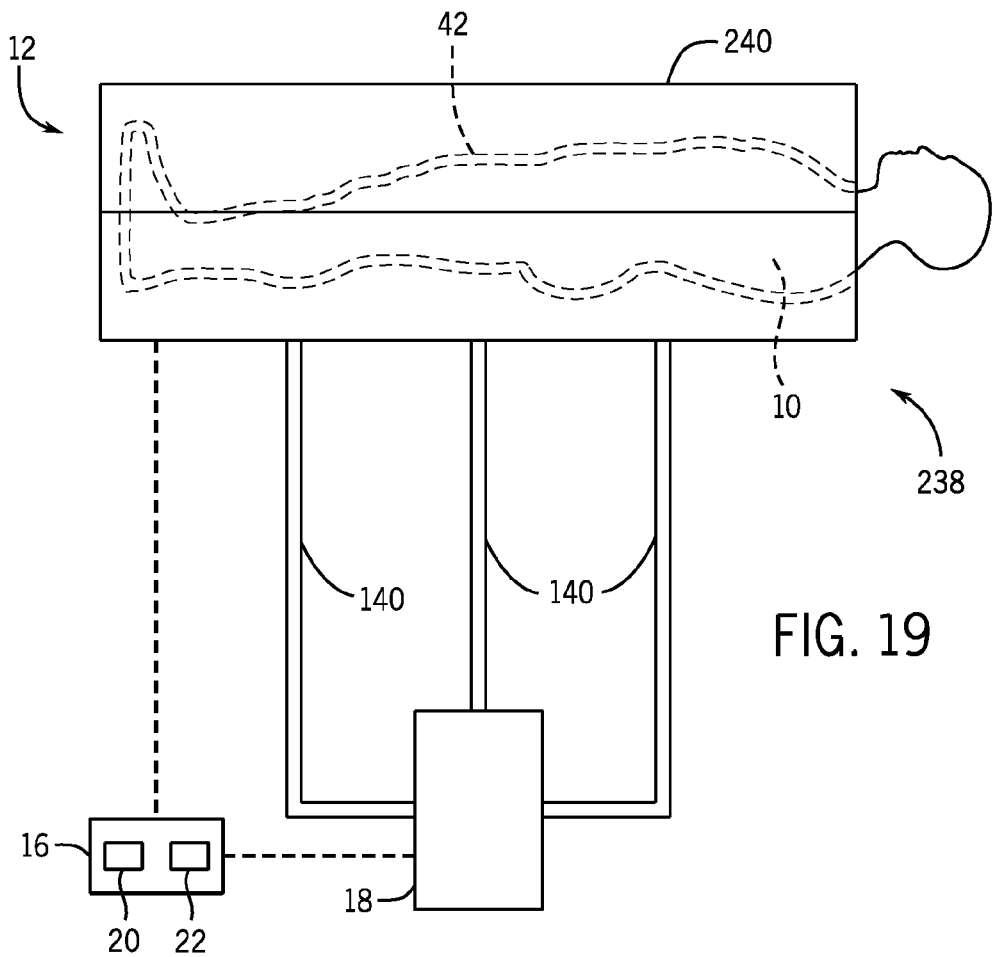
FIG. 19 is a side view of an embodiment of a cold plasma system chamber.

FIG. 19 is a side view of a cold plasma system 12 capable of surrounding most of a patient's body. For example, the cold plasma system 12 may be a patient enclosure 238 defining a chamber 240 that encases the patient from neck to foot. In some embodiments, the cold plasma system 12 may include a flexible dielectric layer 42 that surrounds the patient's body enabling plasma formation adjacent the patient's body and treatment/wound sites. In still another embodiment, a conductive fluid may be pumped into the chamber 240, which conforms the flexible dielectric layer 42 to the patient and treatment/wound sites during plasma treatment. In operation, a patient may lay or stand within the enclosure 238 to receive a cold plasma treatment. In some embodiments, the cold plasma system 12 may pump a specialized working gas from gas source 18 through conduits 140 into the enclosure 238, where the gas is sufficiently energized and converted into cold plasma. In another embodiment, the gas source 18 may convert the gas into cold plasma, which is then pumped into the enclosure 238. In still another embodiment, the flexible layer 42 surrounding the patient's body may couple to the conduits 140 and receive cold plasma and or form cold plasma with gas from the gas source 18. In some embodiments, the flexible layer 42 may be a dielectric barrier layer that enables cold plasma formation from atmospheric gases and/or a working gas between the flexible layer 42 and the patient's skin. In this manner, the cold plasma system 12 may enable a cold plasma treatment of substantially the entire patient 10.

Figure 20:
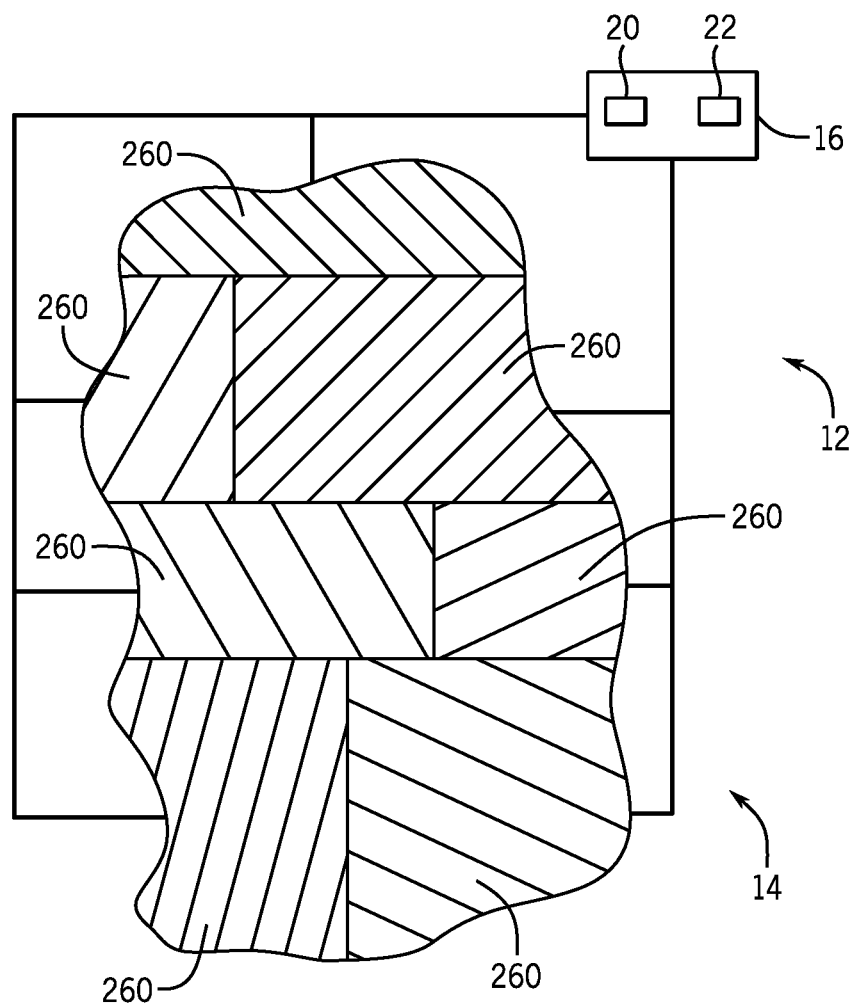
FIG. 20 is a sectional view of a wearable cold plasma applicator taken along line 20-20 of FIG. 1.

FIG. 20 is a sectional view of a wearable cold plasma system 12 that includes a wearable cold plasma applicator 14 with modular interchangeable sections 260. The modular sections 260 may incorporate various combinations of the features shown in FIGS. 1-19, enabling different kinds of cold plasma treatments. For example, the sections 260 may differ in the type of cold plasma produced (e.g., specialized working gas based cold plasma, cold plasma produced from atmospheric gases, or a combination thereof). The sections 260 may also differ in the size and number of apertures 144 that receive a gas; the size and number of plasma generating regions 54; and the arrangement of electrodes 90 and 92 among others. Accordingly, the wearable cold plasma system 12 may enable customized treatment of a particular patient by changing the modular sections 260 on a wearable cold plasma applicator 14.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A system comprising:
a wearable cold plasma system, comprising:
a wearable cold plasma applicator configured to couple to and deliver a cold plasma to a surface of a user wearing the wearable cold plasma device, wherein the wearable cold plasma applicator comprises a multi-layer flexible structure comprising:
a first flexible layer having first opposite sides; and
a second flexible layer having second opposite sides, wherein the second flexible layer extends along the first flexible layer, and the second flexible layer comprises a fluid filled layer, wherein at least one of the first or second flexible layers comprises a dielectric material, wherein an aperture extends at least partially into at least one of the first or second flexible layers.

2. The system of claim 1, comprising a gas source coupled to the wearable cold plasma applicator, wherein the gas source is configured to be ionized and deliver the cold plasma through at least one flow path to the wearable cold plasma applicator.

3. The system of claim 1, wherein the multi-layer flexible structure comprises one or more apertures each associated with one or more electrodes, and the one or more electrodes are configured to generate the cold plasma with a fluid flow through each respective aperture of the one or more apertures.

4. The system of claim 1, wherein the multi-layer flexible structure is configured to conform to the shape of the surface.

5. The system of claim 1, wherein first flexible layer comprises at least one plasma generating region.

6. The system of claim 1, wherein the fluid filled layer holds a conductive fluid.

7. The system of claim 1, wherein the fluid filled layer holds a fluid with conductive particles.

8. The system of claim 1, wherein first flexible layer comprises electrodes in a flexible dielectric barrier material.

9. The system of claim 1, comprising a controller configured to produce an electrical signal that forms cold plasma with the wearable cold plasma applicator, wherein the electrical signal comprises a multi-frequency electrical signal.

10. A system comprising:
a wearable cold plasma system, comprising:
a cold plasma generator configured to generate a cold plasma; and
a wearable cold plasma applicator configured to receive the cold plasma from the cold plasma generator, wherein the wearable cold plasma applicator is configured to couple to and deliver the cold plasma to a user mountable side, wherein the wearable cold plasma applicator comprises a plurality of modular interchangeable plasma application sections configured to selectively couple together to change a configuration of the wearable cold plasma applicator; and
a controller coupled to the cold plasma generator, wherein the controller is configured to produce an electrical signal that forms the cold plasma with the cold plasma generator.

11. The system of claim 10, wherein the wearable cold plasma applicator comprises a multi-layer flexible structure comprising:
a first flexible layer having first opposite sides; and
second flexible layer having second opposite sides, wherein the second flexible layer extends along the first flexible layer, and the second flexible layer comprises a fluid filled layer.

12. The system of claim 11, wherein the fluid filled layer holds a fluid with conductive particles.

13. The system of claim 11, wherein the multi-layer flexible structure comprises one or more electrodes around at least one aperture, and the one or more electrodes are configured to generate the cold plasma with a gas passing through the at least one aperture.

14. The system of claim 10, wherein the electrical signal comprises a multi-frequency electrical signal.

15. The system of claim 10, wherein the cold plasma generator comprises a fluid source and one or more electrodes upstream from the wearable cold plasma applicator.

16. The system of claim 15, wherein the fluid source couples to the wearable cold plasma applicator with a conduit, and wherein the conduit comprises the one or more electrodes configured to generate the cold plasma with a fluid flow passing through the conduit.

17. The system of claim 10, wherein the wearable cold plasma applicator comprises a first portion and a second portion, and wherein the first portion and the second portion are configured to circumferentially surround the substrate.

18. A method comprising:
conforming a multi-layer flexible structure of a wearable cold plasma applicator to a surface, wherein the multi-layer flexible structure comprises first and second flexible layers disposed one over another, wherein at least one of the first or second flexible layers comprises a dielectric material, wherein an aperture extends at least partially into at least one of the first or second flexible layers;
producing an electrical signal with a controller;
flowing a fluid flow from a fluid source to the wearable cold plasma applicator;
generating a cold plasma using the electrical signal and the fluid flow; and
flowing the cold plasma to the surface with the wearable cold plasma applicator.

19. The system of claim 18, wherein generating the cold plasma comprises generating the cold plasma along or upstream of one or more fluid passages coupled to the fluid source.

20. The system of claim 1, wherein the wearable cold plasma system is configured to supply a flow of fluid to the wearable cold plasma applicator during application of the cold plasma to the surface of the user.

21. The system of claim 1, wherein the wearable cold plasma applicator comprises a plurality of modular interchangeable plasma application sections configured to selectively couple together to change a configuration of the wearable cold plasma applicator.

22. The system of claim 1, wherein the wearable cold plasma applicator comprises a sleeve having one or more electrodes configured to generate the cold plasma in the sleeve.

23. The system of claim 1, wherein the wearable cold plasma applicator comprises a plurality of concentric circular electrodes.

24. The system of claim 1, wherein the wearable cold plasma applicator comprises a plurality of substantially parallel electrodes.

25. The system of claim 1, wherein the wearable cold plasma applicator comprises an enclosure surrounding a chamber configured to receive a portion of the user and surround the portion of the user with the cold plasma.

26. A system comprising:
a wearable cold plasma system, comprising:
a wearable cold plasma applicator configured to couple to and deliver a cold plasma to a surface of a user wearing the wearable cold plasma device, wherein the wearable cold plasma applicator comprises one or more apertures each associated with one or more electrodes, and the one or more electrodes are configured to generate the cold plasma with a fluid flow through each respective aperture of the one or more apertures.

27. A system comprising:
a wearable cold plasma system, comprising:
a wearable cold plasma applicator configured to couple to and deliver a cold plasma to a surface of a user wearing the wearable cold plasma device, wherein the wearable cold plasma applicator comprises a plurality of modular interchangeable plasma application sections configured to selectively couple together to change a configuration of the wearable cold plasma applicator, wherein the wearable cold plasma applicator comprises a dielectric material.

28. A system comprising:
a wearable cold plasma system, comprising:
a wearable cold plasma applicator configured to couple to and deliver a cold plasma to a surface of a user wearing the wearable cold plasma device, wherein the wearable cold plasma applicator comprises a multi-layer flexible structure comprising:
a first flexible layer having first opposite sides; and
a second flexible layer having second opposite sides, wherein the second flexible layer extends along the first flexible layer, and the second flexible layer comprises a liquid filled layer.

29. The system of claim 28, wherein the fluid filled layer comprises a saline solution.

30. The system of claim 28, wherein at least one of the first or second flexible layers comprises a dielectric material.

* * * * *